United States Patent [19]

Laruelle

[11] Patent Number: 4,656,024
[45] Date of Patent: Apr. 7, 1987

[54] GALENICAL ADMINISTRATION FORM OF METOCLOPRAMIDE, METHOD FOR ITS PREPARATION AND MEDICAMENT COMPRISING THE NEW FORM

[76] Inventor: Claude Laruelle, Avenue Bellevue, 06270 Villeneuve-Loubet, France

[21] Appl. No.: 607,401

[22] PCT Filed: Oct. 22, 1981

[86] PCT No.: PCT/FR81/00134
§ 371 Date: Jun. 23, 1982
§ 102(e) Date: Jun. 23, 1982

[87] PCT Pub. No.: WO82/01468
PCT Pub. Date: May 13, 1982

Related U.S. Application Data

[63] Continuation of Ser. No. 395,019, Jun. 23, 1983, abandoned.

[30] Foreign Application Priority Data

Oct. 28, 1980 [FR] France .................. 80 23028

[51] Int. Cl.$^4$ .......................... A61K 9/24; A61K 9/28
[52] U.S. Cl. .................................................. 424/497
[58] Field of Search ....................... 424/32, 38, 19, 33

[56] References Cited

U.S. PATENT DOCUMENTS 2,963,402 12/1960 Nalin et al. ..................... 167/82
4,264,574 4/1981 Cherqui et al. ................. 424/20

OTHER PUBLICATIONS

Chem. Abs, vol. 83, No. 14, 10-6-75, p. 427, No. 12077m R. Shekerdzhiiski et al. "Antiemetic Preparation . . . .

Primary Examiner—Shep K. Rose
Assistant Examiner—C. Joseph Faraci
Attorney, Agent, or Firm—Browdy and Neimark

[57] ABSTRACT

A new galenic form with delayed release of METROCLOPRAMIDE, useful for gastric treatment, is formed by microgranules comprising a neutral core formed by a grain of an inert excipient comprising at least two components of the type belonging to the class formed by saccharose, starch, talc, desiccating silica, lactose and stearic acid, this neutral grain being provided with a first layer comprising METOCLOPRAMIDE, then a second outer layer formed by a microporous envelope comprising at least one natural and/or synthetic polymer belonging to the class formed by shellac, gum arabic, ethyl cellulose, cellulose acetophtalate, cellulose triacetate, polyoxyethyleneglycol, the methacrylates, styrene-acrylonitrile copolymer and polyvinylpyrrolidone in successive envelopes.

1 Claim, 3 Drawing Figures

GALENICAL ADMINISTRATION FORM OF METOCLOPRAMIDE, METHOD FOR ITS PREPARATION AND MEDICAMENT COMPRISING THE NEW FORM

This application is a continuation of application Ser. No. 395,019, filed 6/23/83, now abandoned.

The present invention relates to a new galenical preparation of METOCLOPRAMIDE, and the medicament comprising this preparation.

METOLCOPRAMIDE has been known for a number of years. In the dichlorhydrate or monochlorhydrate form it is widely used for treating gastro-intestinal functional troubles such as dyspepsies, gastro-duodenal and biliary dyskinesies, chronic gastritis, gastro-duodenal ulcers and nauseas and vomiting. From the pharmacological point of view, the action of METOCLOPRAMIDE is both central and peripheral.

However, the administration of METOCLOPRAMIDE in its present form presents considerable disadvantages by limiting convenience of use.

For example, it has been noted that the presentation in tablet form causes certain, more particularly gastric, intolerances, which prevents its use by a large category of patients, and which also limits its use for long term treatments.

Furthermore, after each administration, i.e. three of four per day if not more, a succession of rapid increases and decreases of the plasmatic rates has been noted, since the organism is subjected alternately to overdoses and underdoses.

Finally, the disadvantages of the conventional forms have not allowed up to now digestive troubles to be treated requiring extended administration, which on the contrary is possible with the new galenic form of administration of METOCLOPRAMIDE as will be demonstrated hereafter, this new form allowing steady release of the preparation in the organism for sufficiently long periods to allow simply a single unit to be taken daily.

Figure 1:
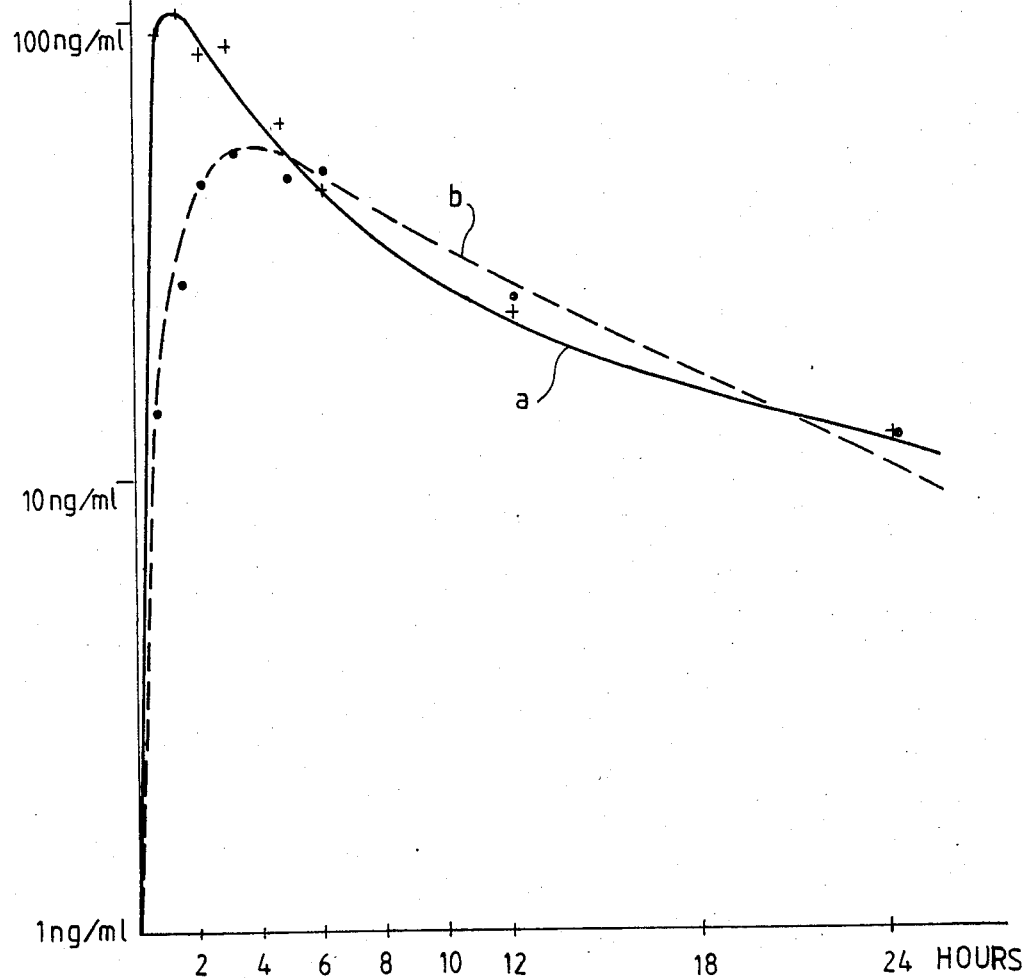
FIGS. 1, 2 and 3 are graphs illustrating the plasmatic concentration of metoclorpramide after oral doses according to the present invention and comparing these graphs with similar graphs showing plasmatic concentration of metoclopramide after conventional dosing.

The present invention has then as object a new galenic form with delayed programmed release of METOCLOPRAMIDE and is characterized in that it is formed by microgranules comprising a neutral core formed by a grain of an inert excipient comprising at least two components of the type belonging to the class formed by saccharose, starch, talc, desiccating silica, lactose and stearic acid, this neutral grain being provided with a first layer comprising METOCLOPRAMIDE, then a second outer layer formed by a microprous envelope comprising at least one natural and/or synthetic polymer belonging to the class formed by shellac, gum arabic, ethyl cellulose, cellulose acetophtalate, cellulose triacetate, polyoxyethyleneglycol, the methacrylates, styrene-acrylonitrile copolymer and polyvinylpyrrolidone in successive envelopes.

In particular, the microporous envelope may be formed from shellac in a proportion by weight varying between 1 and 10% and the inert excipient may be a mixture comprising 40 to 80% by weight of saccharose and 10 to 40% by weight of starch.

According to an advantageous embodiment of the invention, the first layer may comprise from 1 to 20% by weight of METOCLOPRAMIDE, from 0.01% to 0.5% by weight of stearic acid, from 5 to 15% by weight of talc and from 2 to 10% by weight of desiccating silica. Furthermore, the neutral core may comprise METOCLOPRAMIDE adsorbates.

The invention also has as object a process for obtaining the new galenic form remarkable in that neutral sifted and dried microgranules are prepared beforehand, in that a solution in absolute alcohol of METOCLOPRAMIDE is sprayed on these microgranules, in that said microgranules are then coated to form the first layer in one or more coatings, then the microporous envelope is formed by coating with said polymer in solution in a solvent.

Furthermore, the present invention has as object medicaments comprising the new form of administration of METOCLOPRAMIDE in the form of active micrographics mixed with non coated neutral microgranules so as to obtain a predetermined METOCLOPRAMIDE concentration, this assembly of microgranules being presented in the form of capsules, tablets, suppositories, syrup, granules or powder.

The whole of the features and advantages of the invention will be better understood by a man skilled in the art with reference to the following description of particular embodiments taken by way of non limiting examples of the new galenic form, of the process for preparing same and is therapeutical applications, in particular in relation with the pharmacological and clinical tests carried out while using the new galenic form.

EXAMPLE OF PREPARING THE NEW GALENIC FORM

There is given hereafter the manufacturing example corresponding to 100,000 capsules each dosed with 200 mg of METOCLOPRAMIDE chlorhydrate.

(a) MANUFACTURING FORMULA

METOCLOPRAMIDE (monochlorhydrate monohydrate): 2 kg
saccharose
maize starch
stearic acid
shellac
methacrylate polymers
talc
polyvidone
sodium edetate
absolute ethyl alcohol: qs 21 kg

(b) PROCESS OF PREPARATION

Maize starch and saccharose are granulated, then sifted and the grains are subjected to a centrifugal turbine action for a long period to make them perfectly spherical; they are sifted again and completely dried. In a stainless steel mixer, an alcoholic solution of METOCLOPRAMIDE chlorhydrate is sprayed on the neutral cores thus obtained. Then the first layer is formed by incorporating in these microgranules the other excipients with the exception of shellac, then spraying with METOCLOPRAMIDE chlorhydrate is again carried out, this coating being carried out several times with sifting and drying, if necessary, between layers.

When the first layer containing the active ingredient is finished, the outer microporous layer is obtained by spraying on to the granules the shellac in solution in absolute ethyl alcohol.

Then they are carefully dried by eliminating the remaining ethyl alcohol, they are sifted again and the strength of the microgranules obtained is checked, as described hereafter, before being put into capsules, after having adjusted, as necessary, the strength by addition and homogenized with neutral microgranules to obtain the desired strength of 20 mg of METOCLOPRAMIDE.

MEASUREMENT OF THE RELEASE OF METOCLOPRAMIDE

The outer microporous envelope is formed so as to allow theoretical extended release of METOCLOPRAMIDE:

1st hour: release less than 40%
4th hour: release less than 75%
8th hour: release greater than 80%

To check this characteristic, a slaking apparatus is used in which a quantity of microgranules corresponding to about 50 mg of active ingredient are placed in contact with artificial liquids, the apparatus allowing constant stirring and a constant temperature of 37°±0.5° C. to be maintained. The artificial liquids are neutralized solutions with successive pH used according to the following table.

| SOLUTIONS | RELEASE TIME | pH | RESULTS THEORETICAL | OBTAINED |
|---|---|---|---|---|
| 25 ml gastric liquid | 1 hour (1st hour) | 1.5 | <40% | 36% |
| 25 ml intestinal liquid | 1 hour (2nd hour) | 4.5 | >40% | |
| 25 ml intestinal liquid | 2 hours (3rd, 4th) | 6.9 | <75% | 70.8% |
| 25 ml intestinal liquid | 2 hours (5th, 6th) | 6.9 | >75% | |
| 25 ml intestinal liquid | 2 hours (7th, 8th) | 7.2 | >80% | 92.3% |

The new galenic form of the invention has been the subject of a pharmokinetic study in comparison with the conventional tablet form. The study was carried out under cross-over conditions with human subjects. Six subjects of masculine sex each received the two forms spaced apart by two weeks, a capsule with 20 mg of active ingredient containing the microgranules and two 10 mg tablets of conventional form.

The determination of the plasmatic concentrations of METOCLOPRAMIDE was effected by means of ten samples over a 72 hour period.

At the end of the study, the conclusions were the following:

the relative bio-availability is not significantly modified the time of appearance of the serum peak passes from 1 hour to four and a half hours the half-life period passes from about three hours to more than eight hours the two formulations are bio-inequivalent the study of the curves obtained shows that a 20 mg capsule is equal to two, if not three, 10 mg tablets.

So as to illustrate the characteristics of the invention described above, three graphs are presented.

FIG. 1 represents: plasmatic concentrations of metoclopramide after oral doses (6 healthy persons by crossover);

of two 10 mg tablet (prior art); graph a;
of one 20 mg tablet (present application; graph d.

Figure 2:
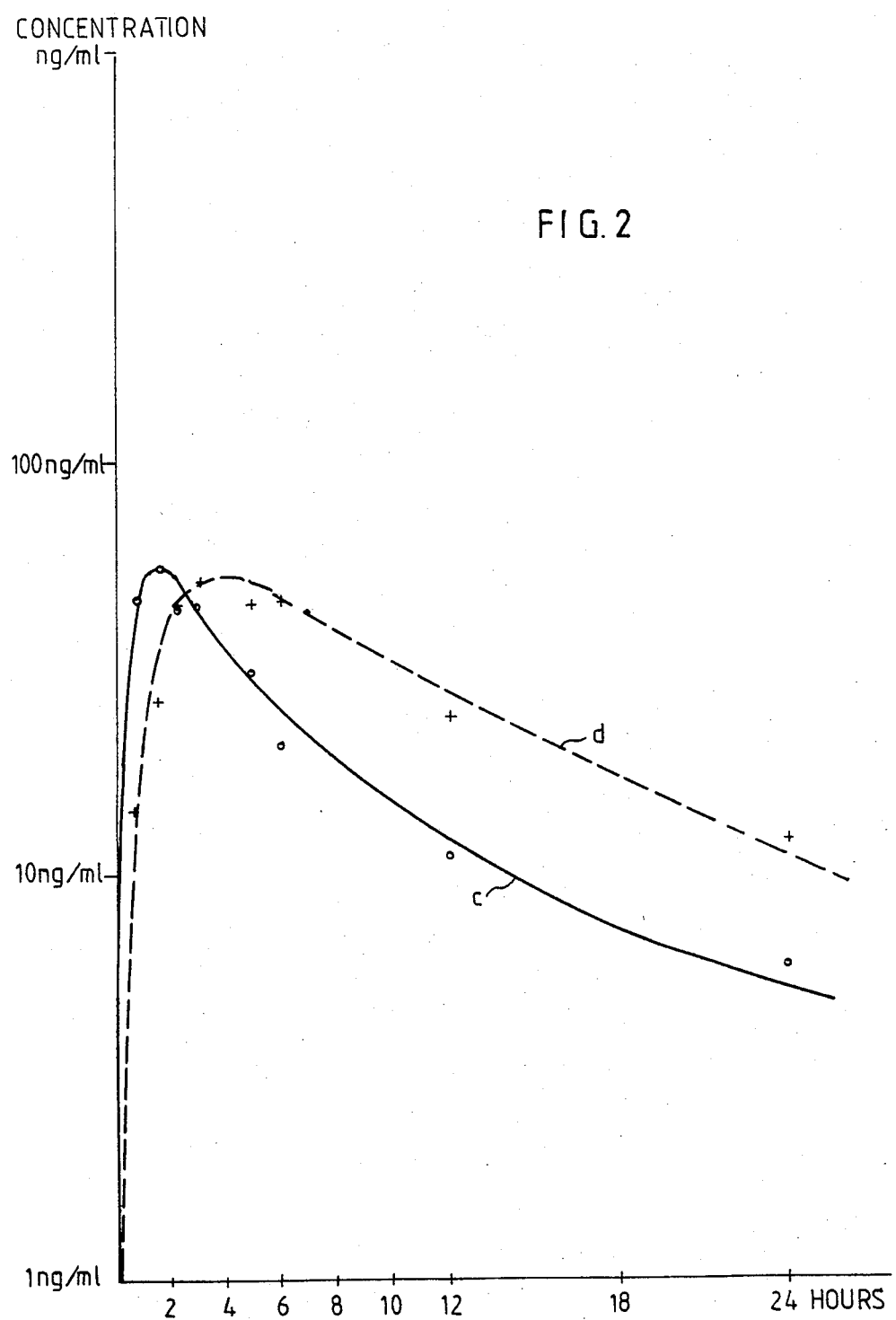

FIG. 2 represents: plasmatic concentrations of metoclopramide after oral doses (6 healthy persons by crossover)

of one 10 mg table (prior art); graph c;
of one 20 mg tablet (present application); graph d.

Figure 3:
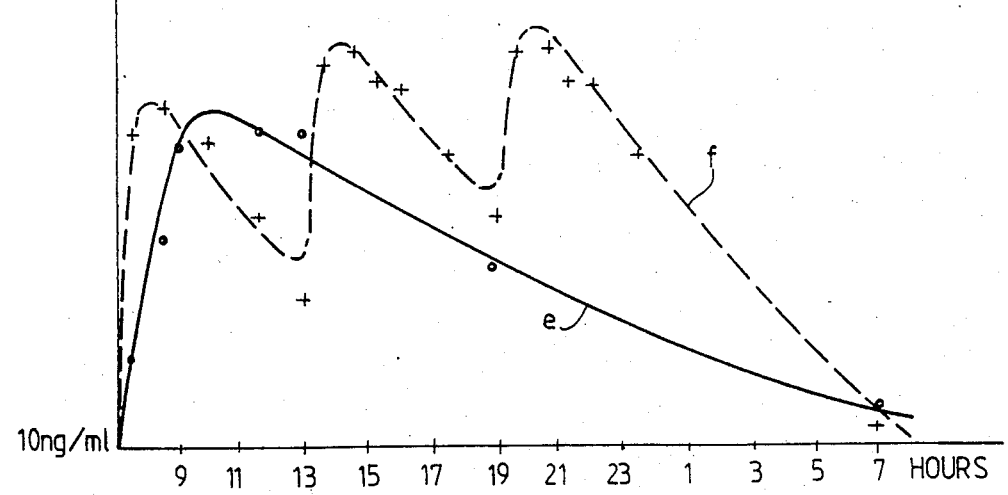

FIG. 3 represents: plasmatic concentrations of metoclopramide after:

graph e one oral doses of a 20 mg tablet (present application);

graph f three oral doses (every six hours) of 10 mg tablets (prior art).

Furthermore, the toxicological study effected on rats has enabled the lethal 50% dose to be determined when the microgranules are administered orally:

in females, the death rate is 50% at 9.2 g/kg
in males, the death rate is 40% at 20 g/kg From the clinical point of view, tolerance of the new presentation was good as a whole and better than the conventional presentation. It thus allows extended treatments to be practiced without appreciable disadvantage for the patient.

Moreover, because of the economy of 35% to 50% dosing of the active ingredient, an improved therapeutical use is therefore obtained justifying the interest of the new galenic presentation.

Consequently, it may be asserted that the new galenic presentation leads to a new useful medicament for the treatment of gastric troubles in general.

It allows controlled release of METOCLOPRAMIDE independently of the way in which the microgranules are administered with a release curve of the active ingredient which is constant from one patient to another and from one dose to another.

Finally, it allows capsules to be made up and ensures the stability of METOCLOPRAMIDE, which is an important industrial and medical improvement.

Of course, a man skilled in the art may find other advantages and variations of the invention, in particular in so far as the process for obtaining microgranules or dosing modifications are concerned, without for all that departing from the scope and spirit of the present invention.

I claim:

1. In a slow-release pharmaceutical composition having a pharmaceutical coated on an inert core material of from 40–80% saccharose and from 10–40% starch, based on the weight of the total composition, to form a spherical coated granule, the coated granule being covered with a semipermeable membrane of methacrylic polymer which progressively releases the pharmaceutical on contact with gastric medium, the improvement wherein comprising:

metoclopramide in an amount of 20 mg, as said pharmaceutical, said metoclopramide being in a first layer, said first layer being 1 to 20% by weight metoclopramide, 0.01% to 0.5% by weight stearic acid, form 5% to 15% by weight talc, and from 2% to 10% by weight dessicating silica, said first layer being coated on the inert core material; and further sequential layers of shellac and methacrylate polymer as the semipermeable membrane, the shellac layer being 1–10% by weight of the total composition.

* * * * *